US00PP13740P29

(12) United States Plant Patent
Flagler

(10) Patent No.: US PP13,740 P2
(45) Date of Patent: Apr. 29, 2003

(54) PLUM TREE NAMED 'DANAE'

(76) Inventor: George Flagler, P.O. Box 68, Parlier, CA (US) 93648

( * ) Notice: Subject to any disclaimer, the term of this patent is extended or adjusted under 35 U.S.C. 154(b) by 0 days.

(21) Appl. No.: 10/013,744

(22) Filed: Dec. 7, 2001

(51) Int. Cl.[7] ..... A01H 5/00
(52) U.S. Cl. ..... Plt./184
(58) Field of Search ..... Plt./184

(56) References Cited

U.S. PATENT DOCUMENTS

PP8,037 P 11/1992 Wuhl

*Primary Examiner*—Bruce R. Campell
*Assistant Examiner*—Susan B. McCormick
(74) *Attorney, Agent, or Firm*—Mark D. Miller

(57) ABSTRACT

A new and distinct variety of plum tree which is somewhat remotely similar to the 'Angeleno' plum (unpatented), but from which it is distinguished therefrom by fruit for harvesting and shipment approximately the three to five days earlier than the fruit produced by the 'Angeleno' plum tree, but which further produces a high quality, fresh market plum of medium size with a dark purple to burgundy colored skin and red flesh of exceptional eating quality and good storage characteristics.

1 Drawing Sheet

BACKGROUND OF THE NEW VARIETY

This present invention relates to a new and distinct variety of plum tree, which will hereinafter be denominated varietally as 'Danae' and more particularly to a plum tree which produces fruit which are mature for commercial harvesting and shipment approximately the first week of September in the San Joaquin Valley of Central California, and which is further distinguished as to novelty by producing a freestone fruit which has a flavor superior that of late maturity commercial plum varieties and which has a coloration having a dark purple to burgundy characteristic and red colored flesh.

There are a number of criteria within which a commercial variety of tree fruit must excel if it is to be a success in the fresh market. Among these are ripening date, flavor, texture, shipping quality and similar characteristics. Another factor or factors are coloration and size of the fruit. Typically fruit that is of high coloration and good size is commercially desirable in that it is attractive and thereby appealing to the consumer. More subtly high coloration, if different than competing commercial variety, attracts immediate attention in the market place which substantially increases the likelihood of commercial success.

Fresh market plums are characterized as the coloration typically by shades of yellowish green to red to dark purple to black with flesh colors varying from yellow or amber to various shades of red. The plum fruit may vary from being a clingstone to semi-freestone to freestone with freestone being the preferred characteristic. Of critical importance in plum varieties of fruit are good size and holding quality along with good eating quality.

ORIGIN AND ASEXUAL REPRODUCTION OF THE NEW VARIETY

The present variety was discovered as an open, pollinated hybrid of the 'Showtime' plum tree (U.S. Plant Pat. No. 8,037) in a sixteen acre plum orchard located approximately ½ mile south of Manning Avenue in Parlier, Calif. The grafting of the scion wood of the new invention took place at that location. The grower has observed this invention since 1999 and confirmed that distinctive characteristics of the parent tree are precisely reproduced in the progeny.

SUMMARY OF THE NEW VARIETY

The 'Danae' plum tree is characterized as to novelty by producing a freestone fruit which has a dark purple to burgundy skin coloration with red flesh. The fruit produced by the 'Danae' plum tree is ripe for commercial harvesting the first week of September in the San Joaquin Valley of Central California. The new and novel variety is perhaps more closely similar to the 'Angeleno' plum tree (unpatented) but is distinguishable therefrom and is characterized as a high quality fresh market plum of medium size ripening in the first week of September and possessing an unusually excellent flavor and excellent handling and shipping characteristics. This new variety is equal to or slightly larger than 'Angeleno' but is substantially superior to the 'Angeleno' in flavor. The new variety has substantially better or richer flavor and is well balanced. The 'Danae' produces fruit about six weeks later than 'Showtime' (U.S. Plant Pat. No. 8,037). The 'Danae' fruit is smaller in size and has better holding capacity than 'Showtime,' and the flesh has a clear ground color as opposed to red for 'Showtime.'

The exterior of this new variety has coloration similar to 'Angeleno' but the flesh has a red coloration and good fumes. Because of the exceptional flavor and the freestone nature this plum will have greater consumer acceptance.

BRIEF DESCRIPTION OF THE DRAWING

The accompanying drawing is a color photograph of mature fruit of the new variety showing several in top view, a second in side elevation displaying the suture, several fruit showing the side thereof 90 degrees from the suture, a fourth sectional along the suture and laid open to expose the stone alone with both halves displaying the stone well, and finally portions of representative foliage, and terminal twigs and branches.

DETAILED DESCRIPTION

Referring more specifically to the pomological details of this new and distinct variety of plum tree, the following has been observed under the ecological conditions prevailing at the orchard of origin which is located at Parlier, Calif. All major color code designations are by reference to the Maerz and Paul, Dictionary of Colors, First Edition, 1930.

TREE

Rootstock: The observed plant was propagated and grown on Nemaguard rootstock.

Size: Medium, similar in size and growth habit to typical plum trees. (approximately 10–12 feet in height, and from approximately 8–10 feet in width, depending upon cultural practices, fertilization, pruning, soil conditions, climate, watering, temperature, girdling and available space).

Vigor: Vigorous, with chilling requirements typical of plum trees grown in the San Joaquin Valley. Very good productivity with regularity of bearing.

Figure (form): Upright to slightly spreading. A. Trunk Size: Medium (typical trunk diameter of approximately 16–18 inches at 18 inches above ground level for mature tree, depending upon age and cultural practices), surface texture semi-rough or coarse with numerous lenticels. Color Code (older bark) Turtle Dove (55-C-2).

Branches:

*Size.*—Medium (typical branch diameter of approximately 8 inches at 40 inches above ground level for mature tree, depending upon age and cultural practices).

*Surface texture.*—Mature — Nearly smooth. Immature — Smooth. Color Code (one year or older) — Kara Dagh (56-A-2). Color Code (immature) — Near Rose Quartz+ (53-C-4). Lenticules — numerous. Lenticels — small.

LEAVES

Size: Medium.

Length: 85–105 mm. (3.35–4.13 inches).

Width: 32–45 mm. (1.26–1.77 inches).

Shape: Lanceolate having a tapering apex and a tapering base.

Texture: Glabrous.

Color code:

*Upwardly disposed surface.*—Mt. Vernon Green (23-J-8).

*Downwardly disposed surface.*—Sage Green (22-J-5).

Marginal form: Serrated.

Leaf vein: Color Code — (Gray drab) Quaker Gray (21-B-1).

Venation pattern: Pinnate.

Thickness: 1 mm. (0.039 inches).

Glandular characteristics:

*Form.*—Globular.

*Color code.*—Mt. Vernon Green (23-J-8).

*Size.*—>1 mm.

*Number.*—2–4 on both sides at base of leaf.

Petiole:

*Size.*—Medium.

*Length.*—15–19 mm. (0.59–0.75 inch).

*Diameter.*—2 mm. (0.079 inch).

*Color code.*—Mt. Vernon Green (23-J-8).

FLOWERS

Flower buds: In clusters of two or three (0.16–0.24 inch).

Size: Small — 4–6 mm. in diameter.

Form: Plump (conic).

Bud scales: Color Code — Green (23-J-9).

Generally: Minutely pubescent.

Date of bloom: Feb. 19–20, 1998 (15–20%).

Size: Small.

Diameter: Width — 15–23 mm. (0.59–0.91 inch diameter).

Bloom quality: Abundant and showy.

Fragrance: None.

Petals:

*Size.*—Five in number. Length: 8–10 mm. long (0.31–0.39 inch). Width: 10 mm (0.39 inch).

*Form.*—Broadly ovate.

*Color code.*—White (2-A-1).

*Apex.*—Semi round.

*Base.*—Semi round.

*Petal claws.*—Broadly truncate. Length — less than 1 mm (0.039 inches). Width — 1 mm (0.039 inches).

*Petal margins.*—Rounded with undulated margins.

*Flower pedicel.*—Very short, 1 mm (0.039 inches). Color Code — Mt. Vernon green (23-J-8). Surface — Slightly pubescent. Diameter — 2 mm (0.079 inches).

Sepals:

*Surface.*—Pubescent.

*Length.*—2–3 mm (0.079–0.12 inches).

*Width.*—3 mm (0.12 inches).

*Form.*—Broadly ovate.

*Color code.*—Green (23-J-9).

*Number.*—Five.

Calyx: Color Code — Brown (11-A-6) at base with a greenish tinge (23-J-8) at apex.

Anthers:

*Size.*—Small.

*Color code.*—Sea Green (11-G-7).

Stamen:

*Size.*—3–6 mm (0.1–0.24 inch long).

*Number.*—16–24.

Pistil:

*Length.*—16 mm (0.24 inch).

*Number.*—1.

*Color code.*—White (2-A-1).

*Surface.*—Pubescent.

FRUIT

Date of maturity: First week of September.

Size: Medium.

*Diameter axial plane.*—55–57 mm (2.17–2.24 inches).

*Transverse in suture plane.*—55–57 mm (2.17–2.24 inches).

*Transverse at right angles to suture plane.*—50–51 mm. (1.97–2.01 inches).

*Average fruit weight.*—3 ounces (4 fruit per 12 ounces).

Form. Uniform, symmetric or asymmetric — slightly asymmetric.

Suture: Shallow.

Ventral surface: Smooth.

Stem cavity:

*Shape.*—Oval.

*Width.*—6–7 mm (0.24–0.28 inch).

*Depth.*—6–9 mm ((0.24–0.35 inch)
*Length.*—10 mm (0.39 inch)
Stem length: Short, caliper — 2 mm (0.079 inch).
Apex: Slightly pointed.
Skin: Medium thickness.
Texture: Soft.
Tendency to crack: None known.
Color codes:
*Blush color.*—Medici Blue (37-E-12).
*Ground color.*—Port (56-E-12). Skin is completely dark.
*Flesh color at maturity.*—Near Rosewood (5-F-10) near skin, then it becomes Afghan R. Checkerberry+ (5-L-6).
*Color of surface of pit cavity.*—Near Rosewood (5-F-10).
*Color of pitwell.*—Ferruginous (5-D-12).
Juice production: Good.
Flavor: Excellent.
Aroma: Good.
Texture: Firm.
Fibers: None.
Ripening: Evenly.
Eating quality: Very good.
Stone: Free.
*Fibers.*—Numbers — Few.
*Size.*—Short. Length — 20–21 mm (0.79–0.83 inch). Width —12–17 mm (0.47 to 0.67 inch). Diameter (thickness) — 11–12 mm (0.43–0.47 inch).
*Form.*—Oval.
*Apex shape.*—Pointed.
*Color code.*—When dry — Sorrel (13-J-11).
*Bases.*—Flat.
*Sides.*—Ridges — 2 shallow ridges on ventral side, one on dorsal side.
*Texture.*—Smooth to slightly pebbled.
*Tendency to split.*—None known.
*Pollination.*—With graft limb of fruit producing tree.
*Use.*—Fresh market.
Quality:
*Ripening quality.*—Uniform.
*Resistance to disease.*—Unknown at this time — normal for plums.
*Shipping and handling qualities.*—Good.

Although the new variety of plum tree has the described characteristics as noted above as a result of the growing conditions prevailing at Parlier, Calif. in the San Joaquin Valley of Central California, it is to be understood that variations of the usual magnitude and characteristics may occur due to changes in growing conditions, fertilization, pruning and pest control.

Having thus described and illustrated my new variety of plum tree, what I claim as new and desire to be secured by plant letters patent is:

1. A new and distinct variety of plum tree substantially as illustrated and described, and which is an unknown sort and is somewhat similar to 'Angeleno' plum tree (unpatented) but is distinguished therefrom and characterized principally as to novelty by producing fruit which are mature for commercial harvesting and shipment during the first week of September, and which have a superior flavor, red flesh, dark purple to burgundy coloration, and excellent eating quality.

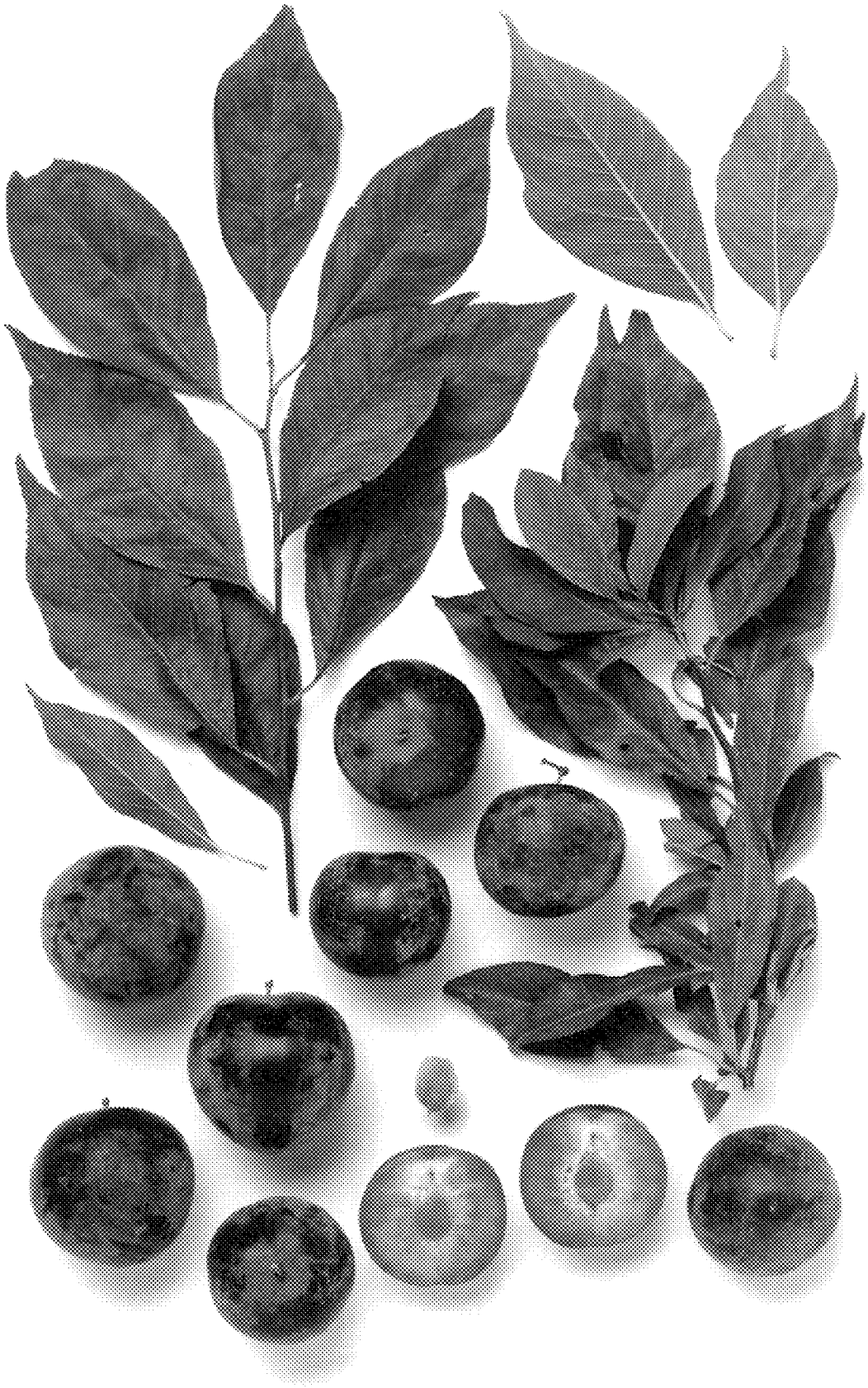

* * * * *